(12) United States Patent
Wang

(10) Patent No.: US 12,721,536 B2
(45) Date of Patent: Sep. 1, 2026

(54) HANDHELD VESSEL STATE MEASUREMENT DEVICE

(71) Applicant: NATIONAL TSING HUA UNIVERSITY, Hsinchu City (TW)

(72) Inventor: Ting-Wei Wang, Hsinchu City (TW)

(73) Assignee: NATIONAL TSING HUA UNIVERSITY, Hsinchu City (TW)

( * ) Notice: Subject to any disclaimer, the term of this patent is extended or adjusted under 35 U.S.C. 154(b) by 163 days.

(21) Appl. No.: 18/742,194

(22) Filed: Jun. 13, 2024

(65) Prior Publication Data

US 2024/0415401 A1 Dec. 19, 2024

(30) Foreign Application Priority Data

Jun. 14, 2023 (TW) ................................ 112122185

(51) Int. Cl.
*A61B 5/0265* (2006.01)
*A61B 5/02* (2006.01)

(52) U.S. Cl.
CPC ........ *A61B 5/0265* (2013.01); *A61B 5/02007* (2013.01)

(58) Field of Classification Search
CPC ..... A61B 5/026; A61B 5/0263; A61B 5/0265; A61B 5/0285; A61B 5/0295
USPC ........................................ 600/504, 506, 507
See application file for complete search history.

(56) References Cited

U.S. PATENT DOCUMENTS

| | | | | |
|---|---|---|---|---|
| 3,560,845 | A * | 2/1971 | Goldberg et al. ........ | G01B 7/32 324/243 |
| 4,621,234 | A * | 11/1986 | Caprihan ............... | A61B 5/026 324/306 |
| 5,309,916 | A * | 5/1994 | Hatschek ........... | A61B 5/02125 600/452 |
| 5,642,734 | A * | 7/1997 | Ruben .................... | G01N 33/49 600/506 |
| 5,935,077 | A * | 8/1999 | Ogle .................... | A61B 5/0265 73/861.12 |
| 7,923,995 | B2 * | 4/2011 | Schulz ................. | G01R 33/365 336/200 |
| 8,180,427 | B2 * | 5/2012 | Phua .................... | A61B 5/0265 600/407 |
| 10,338,029 | B2 | 7/2019 | Nagarkar et al. | |

(Continued)

FOREIGN PATENT DOCUMENTS

| | | |
|---|---|---|
| CN | 101495034 A | 7/2009 |
| CN | 103068302 A | 4/2013 |

(Continued)

*Primary Examiner* — Adam J Eiseman
(74) *Attorney, Agent, or Firm* — Birch, Stewart, Kolasch & Birch, LLP

(57) ABSTRACT

A handheld vascular state measurement device includes a shell, a coil set, and a control module. The shell has a probe part and a handheld part. The coil set is arranged on a measurement surface of the probe part and includes a plurality of coils. The control module is coupled to the coil set. The control module is configured to drive the plurality of coils of the coil set to perform an eddy current induction measurement on a target vessel to derive a plurality of sensing signals corresponding to the plurality of coils. Two of the plurality of sensing signals have a signal characteristic difference. The control module evaluates at least one vascular state of the target vessel based on the signal characteristic difference.

10 Claims, 4 Drawing Sheets

(56) References Cited

U.S. PATENT DOCUMENTS

| | | | | |
|---|---|---|---|---|
| 11,793,596 | B2 | 10/2023 | Agostinelli et al. | |
| 11,806,123 | B2 * | 11/2023 | Hartwell | A61B 5/0536 |
| 2003/0062891 | A1 * | 4/2003 | Slates | G01D 5/2053 324/207.26 |
| 2009/0137900 | A1 | 5/2009 | Bonner et al. | |
| 2009/0203988 | A1 * | 8/2009 | Phua | G01F 1/56 600/409 |
| 2009/0306524 | A1 * | 12/2009 | Muhlsteff | A61B 5/021 600/502 |
| 2010/0219841 | A1 * | 9/2010 | Feldkamp | A61B 5/02007 324/654 |
| 2010/0222696 | A1 * | 9/2010 | Feldkamp | A61B 5/0522 600/547 |
| 2012/0150458 | A1 * | 6/2012 | Sodickson | G01R 33/288 702/57 |
| 2014/0077800 | A1 * | 3/2014 | Frauenrath | G01R 33/5673 324/309 |
| 2015/0045650 | A1 * | 2/2015 | Srinivasa | A61B 5/0265 600/409 |
| 2016/0169838 | A1 * | 6/2016 | Nagarkar | A61B 8/488 324/228 |
| 2018/0143150 | A1 * | 5/2018 | Bezemer | A61B 5/4875 |
| 2019/0240486 | A1 * | 8/2019 | Simon | A61N 1/36025 |
| 2021/0251546 | A1 * | 8/2021 | Tai | A61B 5/02042 |
| 2022/0079442 | A1 | 3/2022 | Piron et al. | |
| 2022/0110539 | A1 | 4/2022 | Bergida et al. | |
| 2025/0186668 | A1 * | 6/2025 | Majerus | A61B 7/04 |

FOREIGN PATENT DOCUMENTS

| | | | | |
|---|---|---|---|---|
| CN | 111885978 | A | 11/2020 | |
| TW | 201632146 | A | 9/2016 | |
| WO | WO-2018108850 | A1 * | 6/2018 | A61B 5/05 |
| WO | WO 2020/056025 | A1 | 3/2020 | |

* cited by examiner 100
112
140
110
130
111
120
1111
150
121
122
123

HANDHELD VESSEL STATE MEASUREMENT DEVICE

TECHNICAL FIELD

The present invention relates to a handheld device for measuring the state of blood vessel; in particular, the present invention relates to a handheld vascular state measurement device which performs the eddy current induction measurement.

BACKGROUND

Peripheral vascular occlusion, also known as arterial stenosis, may cause peripheral limb ischemia, intermittent claudication, ischemic pain, and/or skin ulcers or necrosis in patients. With greasy or high calorie eating habits or abnormal daily routines, the incidence of arterial stenosis will increase. Therefore, there are more and more amputations due to ischemic necrosis in clinical practice. Especially, the issue/problem is common in diabetic patients.

On the other hand, improper weight control, smoking behavior, or high salt/calorie dietary habits can also cause arteries to lose elasticity and become hardening, known as arteriosclerosis. With the acceleration of an ageing society, arteriosclerosis in the elderly often occurs in the lower limb arteries. When there is severe arterial stenosis or arteriosclerosis in the lower limb arteries, it is possible to cause infection in the lower limb wound due to poor blood circulation, and even more so, it may lead to amputation.

Early detection, treatment, and health management will be crucial since neglecting arteriosclerosis or arterial stenosis may lead to serious consequences. However, the initial symptoms of lower limb arterial stenosis or lower limb arterial sclerosis are not obvious and are difficult to detect by the patients themselves. Therefore, universal and fast measurement/monitoring methods will be a major issue of development in the technical field.

In general, ultrasound devices are commonly used in clinical practice to detect whether the blood flow in the lower limb arteries is sufficient or whether there is a problem of embolism or sclerosis. However, the ultrasound devices are large and expensive instruments that are not only inconvenient to carry but also expensive and difficult to popularize. Even though portable ultrasound devices are currently developed, it still needs to be operated by a professional operator and is expensive due to the requirements for sophisticated ultrasound probes and back-end drive/imaging circuits. On the other hand, during ultrasonic measurement, because of the limitations of the ultrasonic measurement mechanism, patients must take off their clothes or pants and apply ultrasonic gel to carry out the measurement, causing distress and discomfort for both medical staff and patients. In addition, after the ultrasonic measurement, the parts coated with the ultrasonic gel must be cleaned or disinfected. Therefore, a non-invasive and non-contact measurement method is necessary to be developed.

SUMMARY

One of the objects of the present invention is to provide a device for measuring the state of blood vessel that is fast and relatively cheap.

One of the objects of the present invention is to provide a device for measuring the state of blood vessel that adopts a non-contact detecting mechanism.

The present invention provides a handheld vascular state measurement device including a shell, a coil set, and a control module. The shell has a probe part and a handheld part. The coil set is arranged on a measurement surface of the probe part and includes a plurality of coils. The control module is coupled to the coil set. The control module is configured to drive the plurality of coils of the coil set to perform an eddy current induction measurement on a target vessel to derive a plurality of sensing signals corresponding to the plurality of coils. Two of the plurality of sensing signals have a signal characteristic difference. The control module evaluates at least one vascular state of the target vessel based on the signal characteristic difference.

Through the handheld vascular state measurement device described above, a non-contact eddy current induction measurement can be performed on a plurality of locations of the target vessel, and feedback signals generated in response to the eddy current induction measurement on the target vessel can be received through a plurality of coils. By comparing the signal differences between the feedback signals from different locations of the target vessel, the vascular state between the different locations of the target vessel can be evaluated. Compared to ultrasound or other measurement means, the handheld vascular state measurement device of the present invention can be made by circuit configurations and a circuit substrate. Therefore, the cost of the handheld vascular state measurement device can be greatly reduced. In addition, the device for measuring the state of blood vessel of present invention has a handheld configuration, that is easy to use and less difficult in learning, making the device be easy to popularize or use at home. Since the eddy current induction measurement is a non-contact measurement mechanism, there is no need to apply ultrasound conductive gel or remove clothing, greatly reducing the inconvenience of the subject or the operator. Accordingly, the handheld vascular state measurement device can be effectively applied in early diagnosis or home care, which enables early detections and treatments of arterial sclerosis or stenosis in the subject, reducing the risk of worsening the condition due to negligence.

BRIEF DESCRIPTION OF THE DRAWINGS

The accompanying drawings are presented to help describe various aspects of the present invention. In order to simplify the accompanying drawings and highlight the contents to be presented in the accompanying drawings, conventional structures or elements in the accompanying drawings may be drawn in a simple schematic way or may be omitted. For example, a number of elements may be singular or plural. These accompanying drawings are provided merely to explain these aspects and not to limit them.

DETAILED DESCRIPTION

Figure 1A:
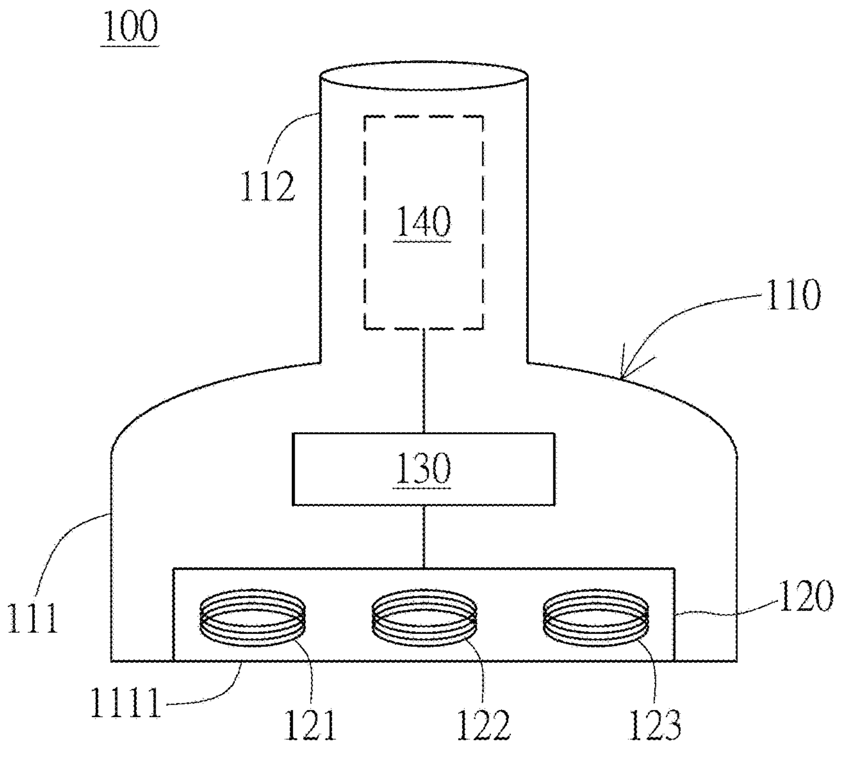
FIGS. 1A and 1B are schematic diagrams of a handheld vascular state measurement device according to an embodiment of the present invention.

Any reference to elements using terms such as "first" and "second" herein generally does not limit the number or order of these elements. Conversely, these names are used herein as a convenient way to distinguish two or more elements or element instances. Therefore, it should be understood that the terms "first" and "second" in the request item do not necessarily correspond to the same names in the written description. Furthermore, it should be understood that references to the first element and the second element do not indicate that only two elements can be used or that the first element needs to precede the second element. Open terms such as "include", "comprise", "have", "contain", and the like used herein means including but not limit to.

The term "coupled" is used herein to refer to direct or indirect electrical coupling between two structures. For example, in an example of indirect electrical coupling, one structure may be coupled with another structure through a passive element such as a resistor, a capacitor, or an inductor.

In the present invention, the term such as "exemplary" or "for example" is used to represent "giving an example, instance, or description". Any implementation or aspect described herein as "exemplary" or "for example" is not necessarily to be construed as preferred or advantageous over other aspects of the present invention. The terms "about" and "approximately" as used herein with respect to a specified value or characteristic are intended to represent within a value (for example, 10%) of the specified value or characteristic.

Referring FIGS. 1A, 1B, 2 and 3, the handheld vascular state measurement device 100 includes the shell 110, the coil set 120, and the control module 130. The shell 110 has the probe part 111 and the handheld part 112. The coil set 120 is arranged on the measurement surface 1111 of the probe part 111. The coil set 120 includes a plurality of coils 121-123. The control module 130 is coupled to the coil set 120. The control module 130 is configured to drive the plurality of coils 121-123 of the coil set 120 to perform the eddy current induction measurement on the target vessel (TV) to derive a plurality of sensing signals (SS1-SS3) corresponding to the plurality of coils 121-123. Two of the plurality of sensing signals (SS1-SS3) have a signal characteristic difference. In an embodiment, any two of the plurality of sensing signals SS1-SS3 will have a signal characteristic difference. The control module 130 calculates at least one vascular state of the target vessel (TV) based on the signal characteristic difference(s) of the sensing signals SS1-SS3.

More specifically, the shell 110 can be produced by conventional technologies such as injection molding, molding, 3D printing, etc. The material of the shell 110 can be plastic or any material commonly used in medical instruments. Preferably, the material of the shell 110 can be metal or a material with magnetic shielding, and the shell 110 can be coated on or attached to non-conductive materials (such as plastic) or a material with magnetic shielding. Therefore, external electromagnetic interference can be reduced. The handheld part 112 of the shell 110 is shaped like a grip for the operator to hold and use. When the handheld part 112 is made by metals or materials with magnetic shielding, the handheld part 112 can reduce the measurement interference and errors caused by the operator's wearing of metal accessories or external electromagnetic waves during measurement. The handheld part 112 may have, for example, an accommodating space for arranging a circuit board or the power module 140 (such as a battery or a power converter, but not limited thereto). The probe part 111 may be wider than the handheld part 112 to accommodate the coil set 120, but not limited thereto. It should be noted that the shape, size, or proportion of the shell 110 shown in FIG. 1A is only for illustrating the present invention, and is not intended to limit the present invention. The size of the probe part 111 is configured to accommodate the coil set 120. In the embodiment shown in FIG. 1A, the probe part 111 may have an accommodating space to accommodate the control module 130 or other circuit structures. However, in another embodiment, the control module 130 may be disposed in the accommodating space of the handheld part 112. The region of measurement surface 1111 of the probe part 111 is configured to arrange the plurality of coils 121-123 of the coil set 120. The measurement surface 1111 of the probe part 111 can be configurated as a flat surface, a curved surface, or a concave surface. In an embodiment, the shape configuration of the probe part 111 can be designed according to the surface shape of the skin where the target vessel (TV) is located under. In another aspect, the measurement surface 1111 in curved or concave shape can provide functions such as focusing and high directionality, making the measurement of the coil set 120 more flexible and accurate.

The coil set 120 includes at least two coils. The coils can be configured in a spiral, circular, or other radiative configurations through a conductor wire to emit electromagnetic signals to the target vessel (TV). The coils may be formed by conductive wires on a rigid or flexible substrate through conventional techniques such as etching, engraving, and photolithography. The plurality of coils included in the coil set 120 can be arranged in a straight line with a fixed spacing or be arranged according to the extension direction of the target vessel (TV). It should be noted that the number of the coils shown in FIGS. 1A and 1B (e.g. 3 coils) is for simplification only, and the number of the coils can be one or more. More specifically, in an embodiment, the coil can be a single coil, and the expected effect of the present invention can be achieved by moving the measurement surface by the operator to obtain two or more measurements as moving.

Figure 1B:
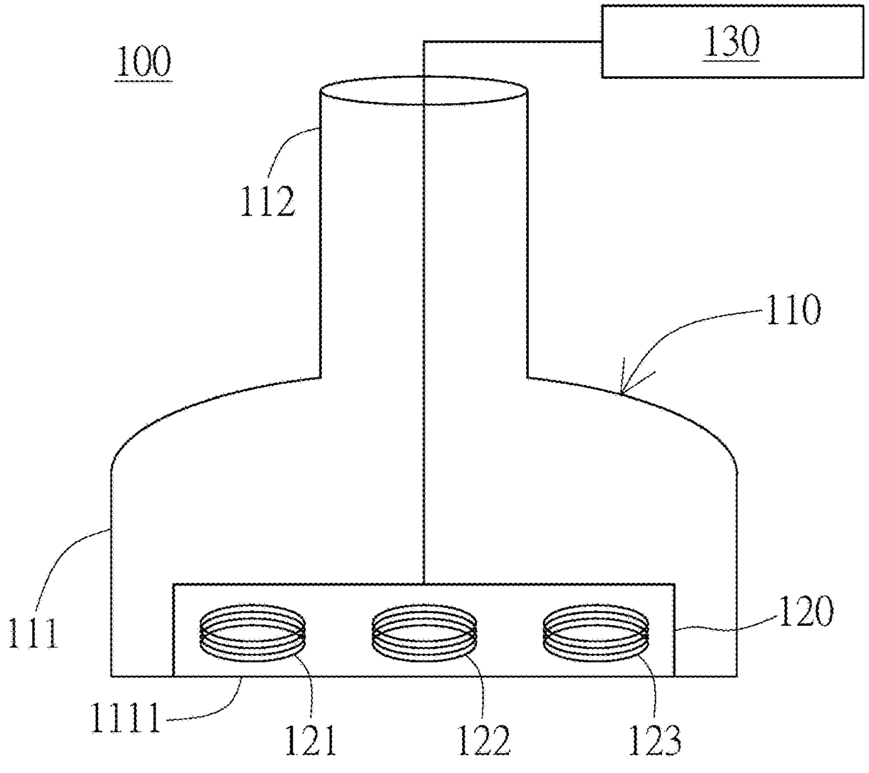

Referring to FIG. 1A, the control module 130 is coupled to the coil set 120. The control module 130 can be a miniaturized integrated circuit component, which is integrated into the shell 110. The control module 130 may be selected from integrated circuits (ICs), such as a system on a chip (SOC) or an application specific integrated circuit (ASIC). The control module 130 may be composed of components integrated on a circuit board and be disposed inside the shell 110 (such as in the accommodating space of the handheld part 112 or the probe part 111). The integration of the control module 130 makes the handheld vascular state measurement device 100 more mobile for easy to carry or home care use. On the other hand, as shown in FIG. 1B, the control module 130 can be an independent module located outside the shell 110. For example, the control module 130 may be selected from a programmable or instrument-controlled module or device such as a computer, a tablet, an industrial computer, an instrument, a FPGA, or a microprocessor, etc. The independent control module 130 will provide benefits such as the selection of the control module with different computing capabilities according to the computing requirements. For example, when a high computing power or regulatory/safety requirements need to be met, a higherend programmable device may be selected as the control modules 130. It should be noted that the control module 130 of the present invention is configured to drive the coil set 120 to perform an eddy current induction measurement on the target vessel (TV). Therefore, in accordance with the disclosure of the present invention, the components of the control module 130 and/or the means for implementing the control module 130 should not be restricted.

Figure 2:
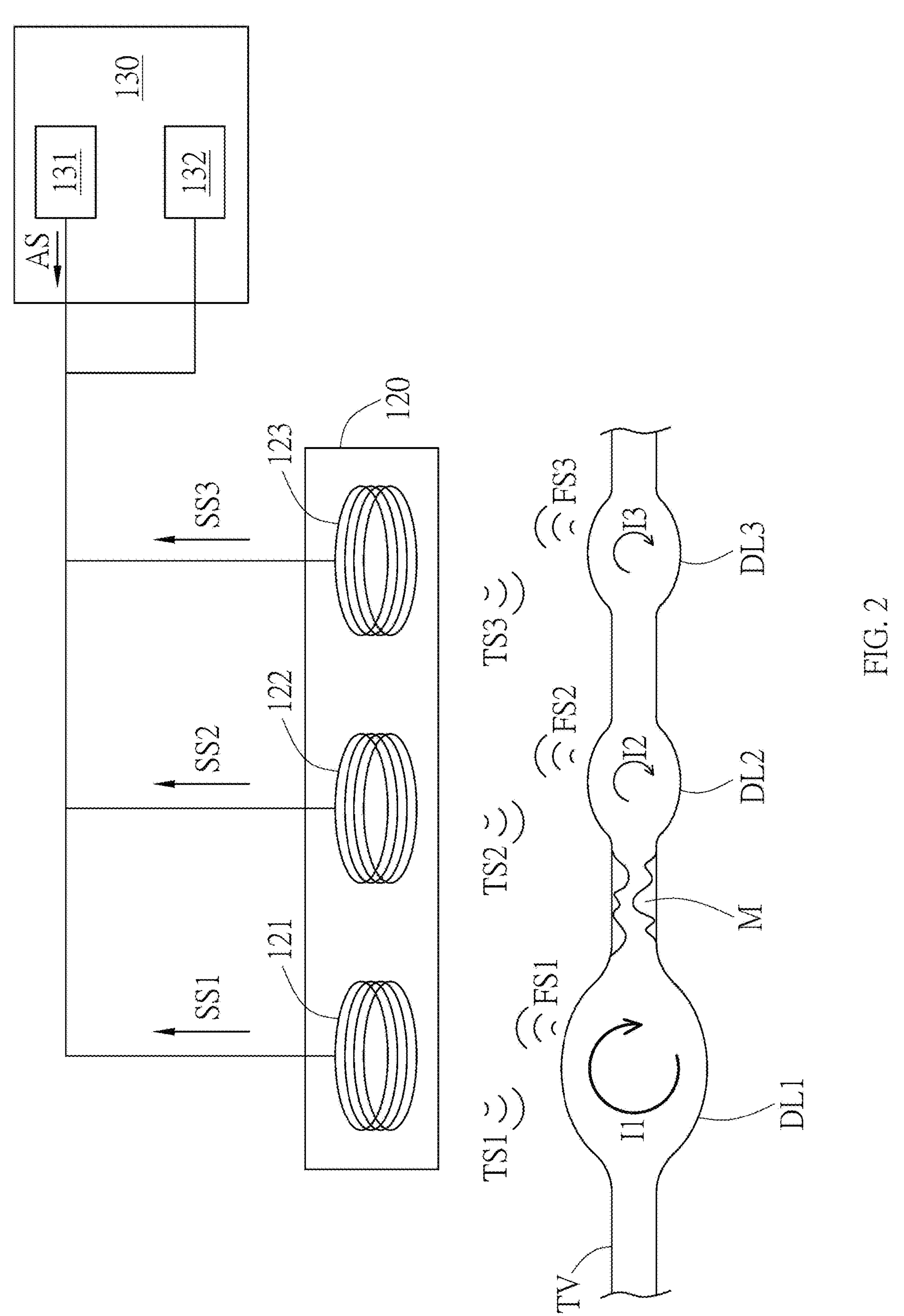
FIG. 2 is a schematic diagram of the eddy current induction measurement according to an embodiment of the present invention.

In an embodiment, referring to FIG. 2, the control module 130 includes the signal generating unit 131 and the measurement unit 132. The signal generating unit 131 is configured to generate the AC signal (AS). For example, the signal generating unit 131 can be an AC/DC signal generating unit composed of active components (e.g. oscillators, or timers) and/or passive components (e.g. resistors, capacitors, or inductors). In an embodiment, the signal generating unit 131 directly generates the AC signal (AS) through active/passive components. In another aspect, the signal generating unit 131 may be configured to convert a DC signal into the AC signal (AS) through circuits of active/passive components. For example, the signal generating unit 131 is configured to oscillate the DC signal through a resonant circuit and output the AC signal (AS). By using the resonant circuit to generate the AC signal (AS), the resonant circuit can achieve benefits of simplifying circuits and saving energy consumption, for example. In the embodiment, the frequency of the AC signal (AS) generated by the signal generating unit 131 is preferably in a range of 1-10 MHz. Therefore, the resonant frequency of the resonant circuit is correspondingly, 1-10 MHz, or the resonant circuit is preferably configured to output the AC signal (AS) of 1-10 MHz.

The plurality of coils 121-123 of the coil set 120 receive the AC signal (AS) from the control module 130, and convert the AC signal (AS) into a magnetic signal and radiate it to the target vessel (TV) due to the electromagnetic effect. For example, when each coil of the plurality of coils 121-123 of coil set 120 receives the AC signal (AS) and outputs the electromagnetic signal (TS1, TS2, or TS3) to the corresponding location (DL1, DL2, or DL3) of the target vessel (TV) to generate corresponding eddy currents (I1, I2, or I3) for the corresponding detection location (DL1, DL2, or DL3). The eddy currents (I1, I2, I3) will generate feedback electromagnetic signals (FS1, FS2, FS3), respectively. The plurality of coils 121-123 of the coil set 120 respectively generate sensing signals (SS1, SS2, SS3) due to the magnetoelectrical effect after receiving feedback electromagnetic signals (FS1, FS2, FS3). It should be noted that the plurality of coils 121-123 of the coil set 120 can be measured simultaneously, or at least two of the plurality of coils 121-123 of the coil set 120 can be selected for measurement using switching means such as switches, selectors, or multiplexers. More specifically, a switch, a selector, or a multiplexer can be coupled between the signal generating unit 131 and the coil set 120 to select coils 121-123 in the coil set 120 to receive the AC signal (AS). On the other hand, the switch, selector, or multiplexer can be coupled between the coil set 120 and the measurement unit 132 to select the sensing signals (SS1-SS3) to be processed. However, the switching means is not limited to the switch, selector, or multiplexer mentioned above. Through the switching means, the amount of the sensing signals that needs to be processed at the same time can be reduced, to reduce energy loss or avoid signal interference that affects the signal resolution or the signal-to-noise ratio.

The measurement unit 132 of the control module 130 is configured to, for example, sample or analog-to-digitally convert the sensing signals (SS1-SS3) and perform calculations or measurements through components with computing ability. The measurement unit 132 performs signal analysis on each of the sensing signals (SS1-SS3) to obtain the frequency, amplitude, or other signal parameters of the sensing signals (SS1-SS3). The measurement unit 132 further analyzes the signal characteristic differences between any two of the sensing signals SS1-SS3, such as the signal characteristic difference $\Delta F_{12}$ between the sensing signals SS1 and SS2, the signal characteristic difference $\Delta F_{13}$ between the sensing signals SS1 and SS3, and the signal characteristic difference $\Delta F_{23}$ between the sensing signals SS2 and SS3. More specifically, when there are N coils included in the coil set 120, the number of analyzed differences in signal characteristics is $$C_2^N.$$

For example, when the number of the coils is two, the number of analyzed difference in signal characteristics is one group. When the number of coils is three, the analysis quantity of signal characteristic differences is three groups.

The measurement unit 132 calculates at least one vascular state of the target vessel (TV) based on the difference in the signal characteristics (i.e., signal characteristic difference). For example, the vascular state can include vascular embolism between the measurement locations, vascular sclerosis, pulse wave velocity (PWV), evaluation of blood flow velocity, etc. More specifically, after transmitting the electromagnetic signals (TS1, TS2, TS3) to the corresponding detection locations (DL1, DL2, DL3) of the target vessel (TV), the blood flow in the detection locations (DL1, DL2, DL3) will be treated as a planar conductor. Therefore, the electromagnetic signals (TS1, TS2, TS3) generate the corresponding eddy currents (I1, I2, I3) at the corresponding detection locations (DL1, DL2, DL3) of the target vessel (TV). The magnitude, frequency, and/or time delay of the eddy currents (I1, I2, I3) may be varied depending on the vascular state of the detection locations (DL1, DL2, DL3). For example, when there is a fat accumulation or thrombus (M) between the first detection location (DL1) and the second detection location (DL2) causing embolism, the blood flow pressures at the first detection location (DL1) and the second detection location (DL2) will be different. The difference of blood pressures will result in different levels of contraction/relaxation of the target vessel (TV) at the first detecting location (DL1) and the second detecting location (DL2), and affect the amplitude of the eddy current (I1) and the eddy current (I2). On the other hand, if there is no fat accumulation or thrombus (M) between the second detection location (DL2) and the third detection location (DL3), the blood flow pressures at the second detection location (DL2) and the third detection location (DL3) of the target vessel (TV) will be similar, making the values of the eddy currents (I2) and (I3) approximate to each other. In another example, the PWV within the target vessel (TV) also affects the time delay of the generation of the eddy current. More specifically, the time delay of the pulse propagation caused by the fat accumulation or thrombus (M) between the first detection location (DL1) and the second detection location (DL2) may be larger than the time delay of the pulse propagation between the second detection location (DL2) and the third detection location (DL3). The signal characteristics of the sensing signal (such as frequency, or time delay) will be varied due to differences in the magnitude or generating time of the eddy current.

Figures 3, 4:
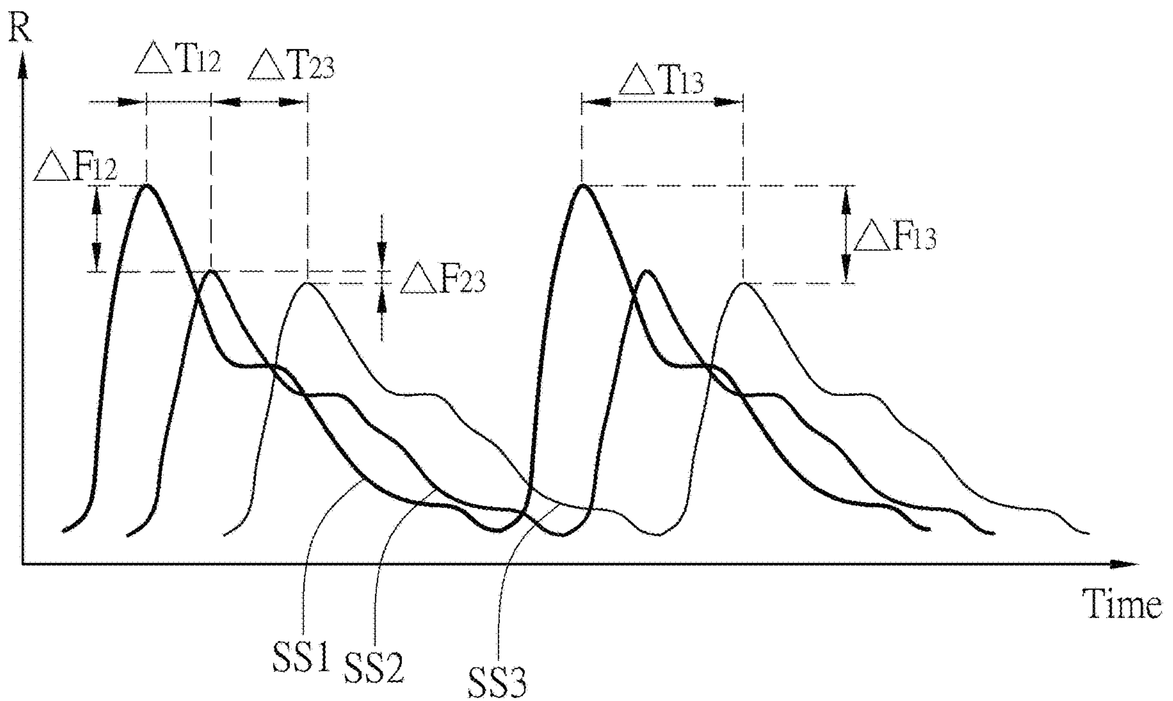
FIG. 3 is a schematic diagram of the difference of signal characteristics between sensing signals according to an embodiment of the present invention.
FIG. 4 is a schematic diagram of the arrangement of the matching component according to an embodiment of the present invention.

The difference in signal characteristics among the sensing signals SS1-SS3 is, for example, shown in FIG. 3, wherein the X-axis represents time or time-dependent data components (such as the $N^{th}$ data), and the Y-axis represents the response R, which is the measurable numerical results of the sensing signals (SS1-SS3) of the plurality of coils 121-123. The measurable numerical result can be amplitude, frequency, frequency change, inductance value, inductance change, or other signal parameters. It should be noted that though 3 groups of sensing signals SS1-SS3 are used for explanation, the number of coils in the present invention is not limited to FIGS. 2 and 3. By measuring the frequency difference ($\Delta F_{12}$, $\Delta F_{13}$, $\Delta F_{23}$) between any two of the first sensing signal (SS1), the second sensing signal (SS2), and the third sensing signal (SS3) due to different eddy currents generated at the different detection locations, the condition of vascular embolism can be determined based on the frequency differences ($\Delta F_{12}$, $\Delta F_{13}$, $\Delta F_{23}$). More specifically, experimental methods such as big data or simulation experiments can be used to identify the relationship curve between the frequency differences $\Delta F$ and the level of vascular embolism. When the frequency difference $\Delta F$ is detected by building a look-up table or other data comparison methods, information on the level of the vascular embolism can be evaluated. On the other hand, the pulse wave velocity $PWV_{nm}$ of the target vessel (TV) among the detection locations (DL1-DL3) corresponding to the coils 121-123 can be determined according to the distance $D_{nm}$ (e.g. $D_{12}$, $D_{13}$, $D_{23}$) between the coils 121-123, and the time delay $\Delta T_{nm}$ (e.g. $\Delta T_{12}$, $\Delta T_{13}$, $\Delta T_{23}$) between the sensing signals (SS1-SS3) corresponding to the coils. More specifically, the PWV can be evaluated using the following formula:

$$PWV_{nm} \cong \frac{D_{nm}}{\Delta T_{nm}}$$

The pulse is generated by the contraction and relaxation transmission of the blood vessels caused by the blood pumped by the heart. When the level of hardening of the blood vessel is higher, it is often accompanied by a higher pulse wave velocity. Therefore, the level of hardening of the target vessel (TV) can be evaluated through the pulse wave velocity (PWV). It should be noted that the above application examples are only used to illustrate the calculation of vascular state in the present invention and are not intended to limit the present invention. Moreover, the calculations of the vascular states of the present invention can be supplemented with parameters such as a heart rate, a blood pressure, the subject's age, or other parameters for corrections to make the evaluation/calculation of the vascular state more accurate. Moreover, in the present invention, the vascular state of the target vessel (TV) can be evaluated by comparing the past and current parameters of the target vessels (TV) through a long-term measurement of the subject.

It should be noted that the present invention is not limited to the type and location of the target vessel (TV). The target vessel (TV) can be any large blood vessel (preferably an artery) on a human body or an experimental subject. In an embodiment, the target vessel (TV) is preferably a lower limb artery (e.g. femoral artery) or an upper limb artery (e.g. brachial artery). Preliminary measurement or long-term observation of the vascular state of the arteries in the limbs can be used to evaluate the level of vascular health or whether there is a potential risk of local ulcers, necrosis, or amputation due to poor peripheral blood circulation.

In an embodiment, referring to FIG. 4, the handheld vascular state measurement device 100 can further include the matching component 150. The matching component 150 is arranged at an outer side of the measurement surface 1111. More specifically, the matching component 150 may be selected from materials with a magnetic impedance between the magnetic impedance of the subject or a medium at an outer side of the subject, and the magnetic impedance of the measurement surface 1111. In this way, the matching component 150 can reduce the energy loss during the transmission of the electromagnetic signals (TS1, TS2, TS3) and/or the feedback electromagnetic signals (FS1, FS2, FS3). With the matching component 150, the goal of providing required signal or improving the signal-to-noise ratio with lower energy will be achieved, and safety issues such as excessive energy causing injury to the subject or insufficient endurance of the device can be avoided. On the other hand, the matching component 150 can be configured to serve as a contact buffer between the measurement surface 1111 and the subject. For example, the matching component 150 can improve the comfort of the subject or the stability during measurement. However, the purpose of disposing the matching component 150 is not limited to the above examples.

Figure 5A:
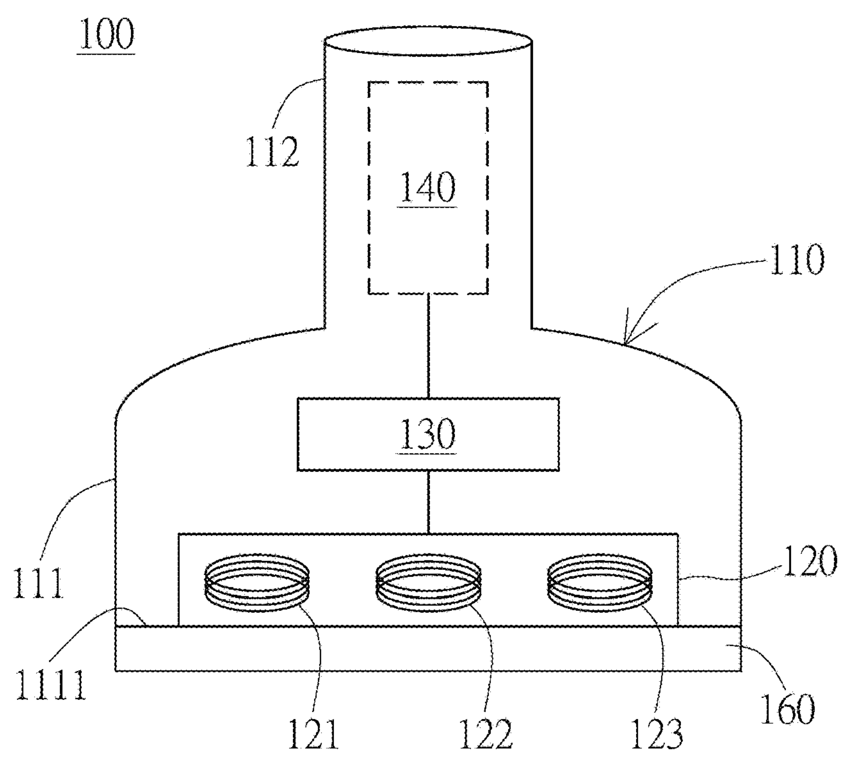
FIGS. 5A and 5B are schematic diagrams of the arrangement of the isolation component according to an embodiment of the present invention.
Figure 5B:
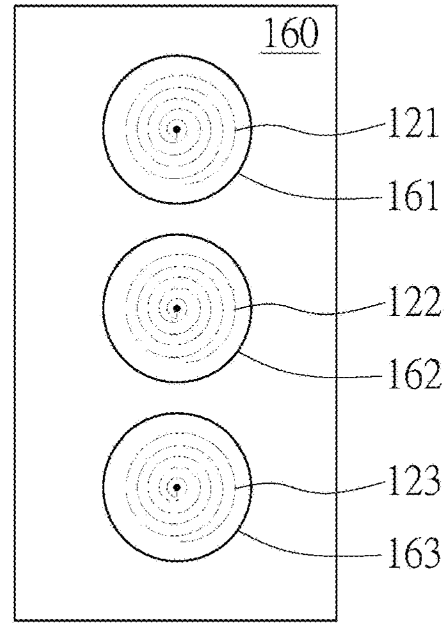

In an embodiment, as shown in FIGS. 5A and 5B, the handheld vascular state measurement device 100 further includes an isolation component 160. The isolation component 160 is located at the outer side of the measurement surface 1111. The isolation component 160 has signal permeable portions 161-163 corresponding to the coils 121-123. The signal permeable portions 161-163 can allow the electromagnetic signals (TS1, TS2, TS3) to pass and reach the subject. The material of the isolation component 160 can be an electrical or magnetic conductor or other materials that can block electromagnetic waves, and the signal permeable portions 161-163 can be openings formed through the isolation component 160 or portions of the isolation component 160 that are made of materials allowing electromagnetic waves to pass therethrough. The electromagnetic signals (TS1, TS2, TS3) are emitted from the coils 121-123 towards the target vessel (TV). However, there are still parts of the emitted electromagnetic signals (TS1, TS2, TS3) that diverge, for example, due to the divergence of magnetic field lines not pointing towards the target vessel (TV). Therefore, the diverged parts of the electromagnetic signals (TS1, TS2, TS3) do not fully (or cannot) act on the detection locations (DL1, DL2, DL3) of the target vessel TV, and even act on other unexpected locations and generate noise. The generated noise may interfere in the accuracy and directionality of the coils 121-123 for the detection locations (DL1, DL2, DL3). By using the isolation component 160, the electromagnetic signals (TS1, TS2, TS3) can be more directional to act on the corresponding detection locations (DL1, DL2, DL3). The isolation component 160 achieves, for example, the goal of improving the signal-to-noise ratio. In addition, the signal permeable portions 161-163 can be shaped as circular openings, square openings, or other shapes based on the shape of the coils 121-123. It should be noted that the shape and/or location of the signal permeable portions 161-163 can be adjusted according to actual needs.

Through the handheld vascular state measurement device 100 as described above, a non-contact eddy current induction measurement can be performed on a plurality of locations of the target vessel (TV). The feedback electromagnetic signals (FS1-FS3) are generated in response to the eddy current induction measurement on the target vessel (TV), and be received by the plurality of the coils 121-123. By comparing the signal differences among the feedback electromagnetic signals transmitted from different locations of the target vessel (TV), the vascular state between different locations of the target vessel (TV) can be evaluated. Compared to the conventional ultrasound or other measurement methods, the handheld vascular state measurement device 100 of the present invention can be made through a circuit configuration and a circuit substrate, and the cost can be greatly reduced. In addition, the handheld vascular state measurement device of the invention is easy to use and less difficult in learning and therefore, is easy to popularize or use at home. Furthermore, the eddy current induction measurement belongs to a non-contact detection mechanism, so there is no need to apply ultrasound conductive gel or remove clothing, greatly reducing the inconvenience of the subject. The handheld vascular state measurement device of the invention can be effectively applied to early diagnosis or home care, enabling early detections and treatments of arteriosclerosis or stenosis and reducing the risk of worsening the condition due to negligence.

The previous description of the present invention is provided to enable a person of ordinary skill in the art to make or implement the present invention. Various modifications to the present invention will be apparent to a person skilled in the art, and the general principles defined herein can be applied to other variations without departing from the spirit or scope of the present invention. Therefore, the present invention is not intended to be limited to the examples described herein, but is to be in accord with the widest scope consistent with the principles and novel features of the invention herein.

What is claimed is:

1. A handheld vascular state measurement device, comprising:

a shell having a probe part and a handheld part;

a coil set arranged on a measurement surface of the probe part, the coil set including a plurality of coils arranged in a line with a fixed pitch along an extending direction; and a control module coupled to the coil set, wherein the control module is configured to drive the plurality of coils of the coil set to perform an eddy current induction measurement on a target vessel to derive a plurality of sensing signals corresponding to the plurality of coils, wherein the control module is further configured to determine a signal characteristic difference between two of the plurality of sensing signals that are derived substantially simultaneously from different locations along the extending direction, and evaluates at least one vascular state of the target vessel based on the signal characteristic difference.

2. The handheld vascular state measurement device of claim 1, wherein the eddy current induction measurement includes:

transmitting a plurality of electromagnetic signals to a plurality of detection locations of the target vessel, respectively; and receiving, by the plurality of coils, a plurality of feedback electromagnetic signals from the plurality of detection locations to obtain the plurality of sensing signals.

3. The handheld vascular state measurement device of claim 1, wherein the signal characteristic difference between the two of the plurality of sensing signals at least includes a frequency difference between the two of the plurality of sensing signals.

4. The handheld vascular state measurement device of claim 1, wherein the signal characteristic difference between the two of the plurality of sensing signals at least includes a time delay between the two of the plurality of sensing signals.

5. The handheld vascular state measurement device of claim 4, wherein two of the plurality of coils are arranged by a distance, and the control module evaluates, according to the time delay and the distance, an evaluated blood flow rate at a measurement region corresponding to the two of the plurality of coils.

6. The handheld vascular state measurement device of claim 1, wherein the target vessel is a femoral artery.

7. The handheld vascular state measurement device of claim 5, wherein the at least one vascular state includes an embolism level or a hardening level of the target vessel at a measurement region corresponding to the two of the plurality of coils.

8. The handheld vascular state measurement device of claim 1, wherein an isolation component is arranged at an outer side of the measurement surface, and the isolation component has a plurality of signal permeable portions corresponding to the plurality of coils.

9. The handheld vascular state measurement device of claim 1, wherein a matching component is arranged at an outer side of the measurement surface, and the matching component is configured to reduce energy loss during transmission of electromagnetic signals between the measurement surface and the target vessel.

10. The handheld vascular state measurement device of claim 1, wherein the control module is arranged inside the shell.

* * * * *